United States Patent
Erickson et al.

(10) Patent No.: US 9,371,349 B2
(45) Date of Patent: *Jun. 21, 2016

(54) LOW TEMPERATURE, VACUUM ASSISTED CHLORINATION OF SUCROSE-6-ESTERS FREE OF OVERCHLORINATED BY-PRODUCTS AS INTERMEDIATES FOR THE PRODUCTION OF THE ARTIFICIAL SWEETENER, SUCRALOSE

(71) Applicant: Lexington Pharmaceuticals Laboratories, LLC, Carmel, IN (US)

(72) Inventors: William Randal Erickson, Carmel, IN (US); Stephen Craig Fields, Fishers, IN (US)

(73) Assignee: Lexington Pharmaceuticals Laboratories, LLC, Carmel, IN (US)

( * ) Notice: Subject to any disclaimer, the term of this patent is extended or adjusted under 35 U.S.C. 154(b) by 49 days.

This patent is subject to a terminal disclaimer.

(21) Appl. No.: 14/245,452

(22) Filed: Apr. 4, 2014

(65) Prior Publication Data

US 2014/0221642 A1   Aug. 7, 2014

Related U.S. Application Data

(63) Continuation of application No. 13/826,493, filed on Mar. 14, 2013, now Pat. No. 8,729,255, which is a continuation of application No. PCT/US2011/061796, filed on Nov. 22, 2011.

(60) Provisional application No. 61/416,674, filed on Nov. 23, 2010.

(51) Int. Cl.

| C07H 1/00 | (2006.01) |
| C07H 5/02 | (2006.01) |
| C07H 13/04 | (2006.01) |
| C07H 13/08 | (2006.01) |
| A23L 1/236 | (2006.01) |

(52) U.S. Cl.
CPC .. C07H 1/00 (2013.01); C07H 5/02 (2013.01); C07H 13/04 (2013.01); C07H 13/08 (2013.01); *A23L 1/2367* (2013.01); *A23V 2250/264* (2013.01)

(58) Field of Classification Search
None
See application file for complete search history.

(56) References Cited

U.S. PATENT DOCUMENTS

| 4,380,476 A | 4/1983 | Mufti et al. |
| 4,435,440 A | 3/1984 | Hough et al. |
| 4,634,784 A | 1/1987 | Nagato et al. |
| 4,762,537 A | 8/1988 | Fleming et al. |
| 4,980,463 A | 12/1990 | Walkup et al. |
| 5,254,153 A | 10/1993 | Mudder |
| 5,498,709 A | 3/1996 | Navia et al. |
| 6,206,950 B1 | 3/2001 | Ireland |
| 6,368,568 B1 | 4/2002 | Lord |
| 6,503,396 B2 | 1/2003 | Kim et al. |
| 6,831,181 B2 | 12/2004 | Bhatia |
| 6,860,985 B2 | 3/2005 | Siskin et al. |
| 6,936,724 B2 | 8/2005 | Ohara et al. |
| 7,262,327 B2 | 8/2007 | Mendelovici et al. |
| 7,425,258 B2 | 9/2008 | Chen et al. |
| 7,626,016 B2 | 12/2009 | Wu et al. |
| 7,741,477 B2 | 6/2010 | Deshpande et al. |
| 7,910,727 B2 | 3/2011 | Li et al. |
| 8,153,849 B2 | 4/2012 | Scherrer et al. |
| 8,530,643 B2 | 9/2013 | Boutzaele et al. |
| 8,729,255 B2 * | 5/2014 | Erickson et al. .............. 536/124 |
| 2004/0030124 A1 | 2/2004 | Catani et al. |
| 2004/0260039 A1 | 12/2004 | Yoshimura et al. |
| 2005/0191396 A1 | 9/2005 | Seltzer et al. |
| 2007/0100139 A1 | 5/2007 | Fry |
| 2007/0207246 A1 | 9/2007 | Wang et al. |
| 2008/0103295 A1 | 5/2008 | Ho et al. |
| 2008/0125584 A1 | 5/2008 | Ratnam et al. |
| 2008/0163867 A1 | 7/2008 | Subramanyam et al. |
| 2008/0227971 A1 | 9/2008 | Leinhos et al. |
| 2008/0234526 A1 | 9/2008 | Scherrer et al. |

(Continued)

FOREIGN PATENT DOCUMENTS

| EP | 1923379 A1 | 5/2008 |
| GB | 2468936 A | 9/2010 |

(Continued)

OTHER PUBLICATIONS

European Patent Office, International Search Report and Written Opinion issued in parent PCT International Application No. PCT/US2011/061796 on Feb. 7, 2012.

European Patent Office, International Search Report and Written Opinion issued in related PCT International Application No. PCT/US2012/060068 on Dec. 18, 2012.

Kresge, Charles T. et al., "Molecular Sieves," *Kirk-Othmer Encyclopedia of Chemical Technology*, vol. 16, John Wiley and Sons, Incorporated, pp. 811-853, pub. Date Oct. 2005 ©2006.

Scherrer, Stephen C. et al. inventors, partial file history of U.S. Appl. No. 11/999,381 (now U.S. Pat. No. 8,153,849) from filed of Dec. 4, 2007 through filing of Response to Final Office Action filed Jul. 11, 2011; 391 pages.

United States Patent and Trademark Office, Office Action issued in related U.S. Appl. No. 13/826,851 on Jul. 15, 2013.

*Primary Examiner* — Eric Olson
*Assistant Examiner* — Dale R Miller
(74) *Attorney, Agent, or Firm* — Leydig, Voit & Mayer, Ltd.

(57) ABSTRACT

Disclosed is a method of chlorinating a carbohydrate or derivative thereof, for example, a sucrose-6-ester at the 4,1', and 6' positions, with irreversible removal of HCl formed during the reaction to form the chlorinated carbohydrate or derivative thereof, for example, a 4,1',6'-trichloro-4,1',6'-trideoxy-6-O-ester of galactosucrose (TGS-6E). The irreversible removal of HCl can be carried out by an irreversible physical process and/or an irreversible chemical process. Sucralose, an artificial sweetener, can be prepared by deesterification of the TGS-6E. The chlorination reaction takes place at low temperatures and the desired chlorinated product is obtained in high yields and in high purities.

27 Claims, No Drawings

(56) References Cited

U.S. PATENT DOCUMENTS

| | | |
|---|---|---|
| 2008/0300391 A1 | 12/2008 | Ratnam et al. |
| 2008/0300392 A1 | 12/2008 | Xu |
| 2008/0300401 A1 | 12/2008 | Xu |
| 2009/0105470 A1 | 4/2009 | Ratnam et al. |
| 2009/0118493 A1 | 5/2009 | Ratnam et al. |
| 2009/0131653 A1 | 5/2009 | Ratnam et al. |
| 2009/0163704 A1 | 6/2009 | Ratnam et al. |
| 2009/0208747 A1 | 8/2009 | Ratnam et al. |
| 2009/0259034 A1 | 10/2009 | Kerr et al. |
| 2009/0259036 A1 | 10/2009 | Wiley, Jr. |
| 2009/0264640 A1 | 10/2009 | Ratnam et al. |
| 2009/0281295 A1 | 11/2009 | Micinski et al. |
| 2009/0299055 A1 | 12/2009 | Wiley, Jr. et al. |
| 2009/0324513 A1 | 12/2009 | Ratnam et al. |
| 2010/0022765 A1 | 1/2010 | Ho et al. |
| 2010/0056773 A1 | 3/2010 | Chandrasekhar et al. |
| 2010/0081803 A1 | 4/2010 | Micinski et al. |
| 2010/0160625 A1 | 6/2010 | Ratnam et al. |
| 2010/0168412 A1 | 7/2010 | Ratnam et al. |
| 2010/0184969 A1 | 7/2010 | Rajadhyaksha et al. |
| 2010/0202570 A1 | 8/2010 | Tsai et al. |
| 2010/0216195 A1 | 8/2010 | Ratnam et al. |
| 2010/0228020 A1 | 9/2010 | Ratnam et al. |
| 2010/0292462 A1 | 11/2010 | Chen et al. |
| 2013/0197213 A1 | 8/2013 | Erickson et al. |
| 2013/0197215 A1 | 8/2013 | Erickson et al. |

FOREIGN PATENT DOCUMENTS

| | | |
|---|---|---|
| WO | WO 2007/054971 A2 | 5/2007 |
| WO | WO 2007/099557 A2 | 9/2007 |
| WO | WO 2008/052076 A2 | 5/2008 |
| WO | WO 2008/096928 A1 | 8/2008 |
| WO | WO 2010/109189 A1 | 9/2010 |
| WO | WO 2010/151489 A1 | 12/2010 |
| WO | WO 2012/071385 A1 | 5/2012 |
| WO | WO 2013/056128 A1 | 4/2013 |

* cited by examiner

LOW TEMPERATURE, VACUUM ASSISTED CHLORINATION OF SUCROSE-6-ESTERS FREE OF OVERCHLORINATED BY-PRODUCTS AS INTERMEDIATES FOR THE PRODUCTION OF THE ARTIFICIAL SWEETENER, SUCRALOSE

CROSS-REFERENCE TO RELATED APPLICATIONS

This patent application is a continuation of copending U.S. patent application Ser. No. 13/826,493, filed Mar. 14, 2013, which is a continuation of International Patent Application No. PCT/US2011/061796, filed Nov. 22, 2011, which claims the benefit of U.S. Provisional Patent Application No. 61/416,674, filed Nov. 23, 2010, the disclosures of which are incorporated by reference in their entireties.

BACKGROUND OF THE INVENTION

Chlorination of carbohydrates and derivatives thereof, such as sugars and their esters, has been known. For example, sucralose, 4,1',6'-trichloro-4,1',6'-trideoxygalactosucrose, is an artificial sweetener with a sweetness intensity many times that of sucrose. Sucralose is a sucrose derivative, made by chlorination of a sucrose ester such as sucrose-6-acetate or sucrose-6-benzoate.

Attempts have been made in the industry to improve the reaction conditions, the yield, and/or the reduce the amount of impurities formed during the chlorination reaction. However, the reaction conditions are still harsh, e.g., high reaction temperatures and/or long reaction times are employed. Alternatively, the yields of the trichlorinated ester are low. In some instances, the reported chlorination reaction conditions are not reproducible.

For example, U.S. Pat. No. 4,980,463 to Walkup et al. discloses that when sucrose-6-benzoate is chlorinated with phosgene, only monochlorinated product is formed within the temperature range of 50° C. to about 70° C. The '463 patent discloses that the reaction mixture may be maintained at this temperature for at least 1 hour with little or no di- or higher chlorination occurring.

The '463 patent further discloses that the above monochlorinated reaction mixture must be heated to a temperature range of 75° C. to 100° C. and preferably 80° C. to 85° C. to effect partial dichlorination of the sucrose-6-ester. The '463 patent discloses that at this temperature little or no tri- or higher chlorination occurs and a mixture of primarily monochlorinated sucrose-6-esters plus some dichlorinated sucrose-6-esters results after about 1 hour. The '463 patent further states that maintenance of the reaction mixture at this temperature for longer periods of time results in a higher degree of conversion of monochlorinated sucrose-6-esters to dichlorinated sucrose-6-esters with little or no trichlorination observed by silica gel TLC.

The '463 patent further states that in preferred aspects of the invention, the temperature is increased rapidly, after initially attaining 80° to 85° C., to a temperature sufficient to completely convert monochlorinated sucrose-6-esters to dichlorinated sucrose-6-esters, trichlorinated sucrose-6-esters and little or no tetra- or higher chlorinated sucrose-6-esters. The '463 patent further teaches that the temperatures for this step are usually in the range of about 100° C. to about 130° C. and preferably from about 110° C. to about 125° C. According to the '463 patent, the reaction mixture is held at this temperature for a period sufficient to maximize trichlorination, e.g., from about 1 hour to about 6 hours, and preferably chlorination of sucrose-6-ester at 85° C. produces a mixture of chlorinated sucrose-6-ester products consisting essentially of 6'-chlorosucrose-6-ester, 4,6'-dichlorosucrose-6-ester, and 1',6'-dichlorosucrose-6-ester. According to the '463 patent, the above mixture must be heated to a temperature not higher than 125° C. for a period of time sufficient to produce a chlorinated product consisting essentially of 1',4,6'-trichlorosucrose-6-ester.

The '463 patent states that it takes nearly 5 to 6 hours of total reaction time to obtain maximum yields of about 60% of sucralose-benzoate as shown in FIG. 7 of the patent. FIGS. 4 and 5 of the '463 patent, disclosing conversion as a function of reaction time with phosphorous oxychloride, indicate that the sucralose-6-benzoate content reaches a maximum at 4 hours at 115° C., and thereafter drops off, with concomitant increase in higher chlorinated products. In Example 5, the '463 patent discloses that, when phosphorous oxychloride is employed as the chlorinating agent, the yield of sucrose-6-benzoate is only 31.9%.

WO 2008/052076 A2 to Ho et al. discloses a process for the preparation of sucralose by the chlorination of sugar with triphosgene. According to Ho et al., paragraph [0008], the chlorination reaction mixture is heated to 110° C. and refluxed at 110° C. for 3 hours. While Ho et al. contemplates at paragraph [0013] that the chlorination reaction may be carried out under vacuum to avoid the oxidation of the reaction mixture by oxygen in ambient temperature, none of the examples ran the reaction under vacuum.

United States Patent Application Publication No. 2007/0100139 A1 by Fry reportedly discloses methods for chlorinating sucrose-6-esters to produce 1',4,6'-trichlorosucrose-6-esters including providing a reaction mixture in a temperature-controlled vessel at a temperature less than about 65° C. (abstract). The methods for chlorinating the sucrose-6-ester according to Fry further include subjecting the chloroformiminium chloride salt, tertiary amide, and sucrose-6-ester reaction mixture to an elevated temperature between about 75° C. and 100° C. for a period of time sufficient to produce a chlorinated product mixture of chlorinated sucrose-6-ester products consisting essentially of 1',4,6'-trichlorogalacto-sucrose-6-ester. In one aspect, Fry recommends maintaining the temperature during chlorination at about 85° C. for about 50 hours to maximize the yield; however, no actual yield value is reported. Fry also teaches that acetic acid may be used to increase the yield of the trichlorinated sucrose ester. However, the present inventors find that some of the assertions made in Fry are not reproducible. The Fry patent application went abandoned for failure to prosecute.

United States Patent Application Publication No. 2007/0207246 A1 by Wang et al. teaches that sugar-6-acetate can be reacted with $PCl_5$ and DMF to obtain sucralose-6-acetate. Wang et al. asserts at paragraph [0040] that trichloroacetonitrile can be used as a catalyst for the chlorination and the temperature of the reaction mixture is raised to 80° C. in 6 hours and maintained there for 3 hours to obtain sucralose-6-acetate. However, the present inventors experienced a reproducibility issue with this method.

In view of the foregoing, there is a desire to have an improved method of chlorinating carbohydrates or derivatives thereof, particularly sucrose esters.

BRIEF SUMMARY OF THE INVENTION

The invention provides methods of chlorinating sucralose-6-esters and intermediates thereof. Thus, in one aspect, the invention provides a method of selectively chlorinating a sucrose-6-ester at the 4,1', and 6' positions with irreversible removal of HCl formed during the reaction to form a 4,1',6'-trichloro-4,1',6'-trideoxy-6-O-ester of galactosucrose (TGS-6E), which can be converted to sucralose by known methods. The irreversible removal can be carried out by an irreversible physical process and/or an irreversible chemical process.

An advantage of the method of the chlorination of the invention is that it can be performed at a lower temperature than previously reported, thereby avoiding the formation of overchlorinated impurities as well as "charred" intractable organic impurities in the intermediates and/or the final product that are often encountered in reactions run at higher temperatures. Removal of HCl also allows the reaction to go nearly to or fully to completion giving higher conversions. The lower temperature, coupled with the higher conversions of the method of the present invention, leads to conservation of natural resources as it requires less energy for each kilogram of TGS-6E—the immediate precursor to sucralose—produced.

Thus, the present invention offers one or more of the following advantages: greater selectivity, higher yield, reduced amount of impurities, and/or reduced energy consumption during reaction.

DETAILED DESCRIPTION OF THE INVENTION

The present invention provides a method for chlorinating a carbohydrate or a derivative thereof comprising reacting the carbohydrate or derivative thereof with a chlorinating agent and irreversibly removing hydrogen chloride produced during the chlorination of the carbohydrate or derivative thereof.

In accordance with the invention, any suitable carbohydrate or derivative thereof, which has at least one, two, three, four, five, or more hydroxyl groups, of which at least one hydroxyl group is available may undergo chlorination. The carbohydrate can be a monosaccharide, oligosaccharide or polysaccharide. The oligosaccharide can be disaccharide, trisaccharide, tetrasaccharide, or a higher saccharide. An example of a disaccharide is sucrose. Examples of higher saccharides include starches, cellulose, hemicelluloses, gums, dextrans, gellan, pullulan, scleroglucan, welan, xanthans, agars, algins, carrageenans, furcellarans, pectins, chitins, and chitosans.

In accordance with an embodiment of the invention, the carbohydrate or derivative thereof is a sugar or derivative thereof. Examples of suitable sugars include sucrose, maltose, lactose, erythrose, threose, ribose, arabinose, xylose, lyxose, allose, altrose, glucose, mannose, gulose, idose, galactose, and talose, particularly sucrose.

The carbohydrate or sugar derivative can be any suitable derivative, for example, an ester, ether, acetal, carboxyalkylate, or amino, or where an aldehyde or carbonyl group has been reduced or oxidized to hydroxyl or where a hydroxyl group has been removed by reduction or oxidized to a carbonyl or carboxyl group. In an embodiment, the sugar derivative is a sugar ester, more particularly a sucrose ester. In an embodiment, the carbohydrate derivative can also be a nucleoside, e.g., uridine, deoxyuridine, adenosine, deoxyadenosine, guanosine, deoxyguanosine, thymidine, deoxythymidine, cytidine, deoxycytidine, or a nucleotide such as DNA or RNA. In accordance with the invention, the carbohydrate derivative can be one where a carbohydrate molecule is covalently linked another molecule, e.g., a polymer molecule.

In accordance with an embodiment of the invention, the sugar ester is a sucrose-6-ester and the chlorinated product is chlorinated sucrose-6-ester, particularly 4,1',6'-trichloro-4,1',6'-trideoxy-6-O-ester of galactosucrose (TGS-6E). TGS-6E can be prepared by esterification of sucrose. Any suitable ester can be prepared which will be stable to the chlorinating agent that will be used and which can be hydrolyzed without much difficulty. The ester can be a $C_1$-$C_{18}$ aliphatic, $C_6$-$C_{14}$ aryl $C_1$-$C_{18}$ aliphatic or $C_6$-$C_{14}$ aryl carboxylate ester. Particularly suitable carboxylate esters include lower alkyl, e.g., $C_1$-$C_6$ alkyl carboxylates such as acetates and propionates, and $C_6$-$C_{10}$ aryl carboxylates such as benzoate or naphthoate ester. The ester can be prepared by acylation of the carbohydrate or sugar using an acylating agent of the relevant acid, and in the case of carboxylic acylation, it is an acyl anhydride or acyl halide. Alternatively, the carbohydrate can be esterified by enyl esters. In an embodiment, reaction with enyl esters is effected in the absence of water and in the presence of no more than a trace of a base catalyst, for example, in a polar aprotic solvent. For these and other methods of production of esters, see, e.g., U.S. Pat. No. 4,380,476, the disclosure of which is incorporated herein by reference.

In an embodiment, the sucrose ester is sucrose-6-acetate, wherein the acetyl group is placed exclusively at the 6-position. Mono-acylation can be maximized by controlling the reaction, e.g., by maintaining the sucrose in excess throughout the addition of the acylating agent or by using very low reaction temperature. Thus, for example, sucrose can acetylated by the use of acetic anhydride and pyridine at a temperature below about −20° C., e.g., −20 to −75° C., in embodiments, from −25 to −45° C.; see, e.g., U.S. Pat. No. 4,380,476; col. 3, lines 3-37.

In accordance with an embodiment of the invention, the carbohydrate or derivative thereof, particularly, the sugar ester is chlorinated by reacting with a chlorinating agent. Any suitable chlorinating agent can be employed. In accordance with an embodiment, the chlorinating agent is selected from the group consisting of thionyl chloride, sulfuryl chloride, phosgene, phosphorus pentachloride, oxalyl chloride, methane sulfonyl chloride, and bis(trichloromethyl)carbonate.

In accordance with an embodiment, the chlorinating agent is a Vilsmeier reagent having the formula: $[XYC=N^+R_2]$ $Cl^-$, wherein X is hydrogen or alkyl which is optionally substituted with a halogen, alkoxy, thioalkoxy, amido, or cyano; Y is a leaving group; and R is hydrogen, aryl, or $C_1$-$C_{18}$ linear or branched alkyl group or $C_3$-$C_{18}$ cyclic alkyl group, each of which is optionally substituted with halogens, further alkyl chains or heteroatoms. For example, in an embodiment, R is hydrogen, aryl, or alkyl, wherein the aryl or alkyl is optionally substituted with halogen, alkoxy, thioalkoxy, amido, or cyano.

The Vilsmeier reagent can be obtained for example by reaction of thionyl chloride, triphosgene, or any acid chloride with an amide and used either as is or pre-reacted with a heteroatomic nucleophile YH to form an alternative comparably reactive reagent. Such a reagent can alternatively be formed prior to use in the chlorination reaction, or it may be formed in situ or it may be purchased from commercial sources.

In an embodiment, Y is halogen, heteroalkyl or other group capable of being displaced by a heteroatomic nucleophile, tosylate, brosylate, besylate, nosylate, mesylate, alkylfluorosulfonates, triflates, nonaflates, and tresylates, and in an embodiment, Y is halogen.

In a particular embodiment, the method is carried out by employing a Vilsmeier reagent wherein X is hydrogen, Y is chloro, and R is methyl.

In accordance with an embodiment, the Vilsmeier reagent can be produced by the reaction of N,N-dialkyl formamide, e.g., N,N-dimethylformamide, or N,N-dialkylacetamide, e.g., N,N-diemthylacetamide, with a chlorinating agent, in an embodiment, thionyl chloride.

In accordance with the invention, the chlorination reaction can be carried out in a suitable solvent, polar or non-polar, and in an embodiment, polar solvent, particularly polar aprotic solvent. Examples of polar aprotic solvents include N,N-dimethylacetamide, N,N-dimethylformamide. N-methyl pyrrolidone, dimethylsulfoxide, sulfolane, tetrahydrofuran, and combinations thereof, particularly N,N-dimethylformamide. Examples of non-polar solvents include aromatic hydrocarbons, halogenated hydrocarbons and combinations thereof. Examples of aromatic hydrocarbons include xylenes, toluene, and diethyl benzene, and examples of halogenated hydrocarbons include 1,2-dichloroethane, 1,1-dichloromethane, 1,1,2-trichloroethylene, chlorobenzene, and dichlorobenzenes, and combinations thereof.

For example, the sucrose-6-ester and the chlorinating agent are combined in the solvent at a suitable temperature, for example, between $-30°$ C. and $25°$ C. During the addition of the chlorinating agent, the temperature is generally not allowed to rise above about $60°$ C., and in embodiments, above $50°$ C. Typically, the temperature is maintained from about $0°$ C. to about $30°$ C.

The term "irreversibly removing" refers to a process or step wherein the hydrochloride is removed from the reaction mixture such that it is no longer available to come in contact with, remain in the proximity or vicinity of, set up an equilibrium with, interfere or interact with, one or more of the components of the reaction mixture. This is distinct from processes such as the use of entrainment or other trapping method for removing HCl which upon heating or under vacuum releases HCl back into the system.

In accordance with the invention, at least a portion of the HCl produced during the chlorination is removed by an irreversible process. For example, at least about 10%, at least about 20%, at least about 30%, at least about 40%, or at least about 50%, or more, of the HCl produced is removed irreversibly. In an embodiment of the invention, in order for the chlorination to proceed to completion or close to completion, a majority of, all, or substantially all of the HCl produced during the chlorination reaction is irreversibly, and, in embodiments, completely or substantially completely, removed from the reaction mixture. Thus, for example, at least about 60%, about 70%, about 80%, about 90%, about 99%, about 99.9%, or about 99.99% or even 100%, of the HCl is removed irreversibly.

The irreversible removal process can be an irreversible physical process or an irreversible chemical process or a combination thereof.

In an embodiment, at least a portion of the hydrogen chloride is irreversibly removed by an irreversible physical process. Any suitable irreversible physical process can be employed. For example, the irreversible physical process includes applying vacuum or sonic energy to the reaction mixture, sparging a moisture free gas through the reaction mixture, inducing cavitation into the reaction mixture, distilling off HCl, or a combination thereof. The HCl can distill off as a pure component or in combination with one or more other reagents or solvents, e.g., as an azeotrope.

Alternatively, or in addition, in accordance with an embodiment, all or substantially all HCl produced during the chlorination reaction is removed by an irreversible chemical process. The irreversible chemical process can be one which irreversibly reacts with HCl, such as propylene oxide, olefins, and the like, to form an inert substance (like a halocarbon), to bring about the separation and removal of the HCl away from the reaction mixture. Inert substance indicates that the chlorine present in the substance is not available for reaction with the sugar derivative.

Herein, irreversible removal, irreversible physical removal or irreversible chemical process removal does not refer to the use of adsorbents or absorbents in contact with the chlorination reaction mixture to remove the HCl, for example, zeolites, activated carbon or charcoal, or amine reagents such as monoamines or polyamines where attractive or van der Waals forces play a role between the adsorbent or absorber and HCl. In non-physical adsorptive or absorptive processes, the HCl is adsorbed or absorbed by the adsorbent or absorbent; however, the HCl is still present in contact with the reaction medium or in close proximity to the reactants.

Without wishing to be bound by any theory or mechanism, it is believed that the HCl present in the reaction medium, even if present adsorbed or absorbed as in the prior art processes, becomes available to participate in the equilibrium reaction between the substrate to be chlorinated and the chlorinated product. It is believed that the HCl present in the prior art reaction mixture shifts the equilibrium towards the non-chlorinated substrate. In contrast thereto, and in accordance with the invention, the HCl is removed irreversibly from the reaction medium, for example, by an irreversible physical process or by an irreversible chemical process, thereby shifting the equilibrium towards the chlorinated product essentially completely.

In an embodiment of the irreversible physical process, a vacuum is applied to the reaction vessel containing the reaction mixture to remove the HCl formed therein. Any suitable vacuum can be applied, for example, from about 0.01 mm Hg to about 750 mm Hg, and in certain embodiments from about 0.1 mm Hg to about 300 mm Hg, and in some embodiments, from about 1 mm Hg to about 100 mm Hg. The vacuum can be applied for any suitable length of time, e.g., from 1 minute to about 6, 8, 10, or 12 hours or more, and in certain embodiments, from about 5 minutes to about 3 hours, and in some embodiments, from about 30 minutes to about 2 hours. The degree of vacuum that is applied will depend on the temperature of the reaction mixture and the volatility of the solvents present in the reaction mixture. Less volatile solvents allow the application of higher vacuums than more volatile solvents. In some cases solvent distills off and is collected.

In an embodiment, vacuum can be applied to the reaction mixture until all carbohydrate or derivative thereof, e.g., sucrose ester, has been consumed.

In accordance with the invention, the vacuum can be applied when the reaction mixture is being heated or when the reaction mixture has reached the desired reaction temperature.

In accordance with the invention, HCl produced during chlorination can be removed by an adsorbent which is located external to the chlorination reactor. The adsorbent can be placed in a column, tank, or any other type of scrubbing vessel, and HCl vapors or a mixture of HCl and solvent vapors passed through the adsorbent. Thus, the adsorbent contacts the distillate from the chlorination reactor but not the chlorination mixture. The adsorbent can be any suitable adsorbent, for example, an adsorbent comprising an acid scavenger.

The temperature of the reaction mixture is then raised and maintained at a high level for a suitable period of time, e.g., for about 1 to about 16 hours, typically for about 6, 8, 10, 12, or 16 hours. The reaction can be carried out at any suitable temperature. In accordance with an embodiment of the invention, the reaction is performed at a temperature no higher than $100°$ C., as this is the temperature at which over-chlorinated by-products begin to form in significant amounts, and in embodiments, no higher than 90° C., and in further embodiments, no higher than 85° C. In accordance with an embodiment, the highest temperature that can be maintained is about 50° C. to about 60° C. In certain embodiments, the highest temperature that can be maintained is about 75° C. to about 80° C. The reaction mixture can be heated in any suitable manner including heating ramps and/or spiking of temperature. In embodiments, the reaction can be carried out at temperatures even higher than 100° C., for example, 110° C., 120° C., or more for limited periods of time. The extent of the reaction can be monitored by any suitable technique, e.g., TLC and/or HPLC.

One of the advantages of the present invention is that sucralose-6-ester can be produced in high yields and/or high purities, and/or at low temperatures and/or at short reaction times. In this regard, the present invention is superior to known processes.

In accordance with an embodiment of the invention, even while physically or chemically irreversibly removing the HCl produced, e.g., by applying vacuum, sparging with a moisture free gas, sonicating and/or subjecting the reaction mixture to chemical methods for reacting HCl to irreversibly form an inert substance, the reaction mixture can be maintained under a moisture free gas atmosphere. Any suitable moisture free gas can be provided, e.g., argon, nitrogen, helium, or air. The moisture free gas is preferably an inert gas or a gas with minimal reactivity to the reactants and/or the products.

Although the method of the invention does not require that an adsorbent or absorber for HCl be included in the reaction mixture where HCl is formed, in an embodiment, such an adsorbent or absorber can be optionally included in the reaction mixture. For example, the adsorbent or absorber can be an acid scavenger such as zeolites, activated carbon, organic amines, and polymeric resins. For additional examples of adsorbents or absorbers, see International Patent Publication WO 2007/099557 A2, the disclosure of which is incorporated by reference.

After the chlorination reaction, the reaction mixture is quenched. Any suitable quenching reagent can be used, e.g., a mixture of pyridine and water or a mixture of aqueous ammonium hydroxide and methanol. The resulting TGS-6E product is recovered, e.g., by filtering the solution through a bed of adsorbent (e.g., celite), extracting the neutralized aqueous mother liquor with an appropriate solvent, and concentrated, e.g., by drying under vacuum to a viscous oil. The oil may solidify on standing in embodiments of the invention.

In accordance with an embodiment of the invention, the yield of the sucralose-6-ester, particularly sucrose-6-acetate, is at least 65%, in embodiments, at least 70%, and in certain embodiments, at least 80%, and in some embodiments, the yield is as high as 90%. In accordance with an embodiment, the yield is between 65 and 80%, which is a major process improvement over known methods.

In accordance with the invention, the chlorinated sucralose-6-ester isolated by the method is free or substantially free of tar or charred residues, e.g., tar or charred residues are less than 5% by weight, in certain embodiments, less than 1% by weight, and in other embodiments, less than 0.5% by weight.

In accordance with the invention, the sucralose-6-ester produced by the method is free or substantially free of over-chlorinated products. Thus, for example, the over-chlorinated products, e.g., tetrachlorinated sucrose products, are less than 5% by weight, in certain embodiments, less than 1%, and in other embodiments, less than 0.5% by weight.

In accordance with the invention, the sucralose-6-ester produced by the method is free or substantially free of under-chlorinated products. Thus, for example, the under-chlorinated products are less than 10%, less than 5% by weight, in certain embodiments, less than 1%, and in other embodiments, less than 0.5% by weight. In accordance with an embodiment of the invention, the dichlorinated products are less than 4% by weight, in certain embodiments, less than 0.5%, and in other embodiments, less than 0.2% by weight.

In accordance with an embodiment, the invention provides a method for chlorinating a carbohydrate or a derivative thereof comprising:

(i) dissolving the carbohydrate or derivative thereof in a polar or non-polar aprotic solvent to obtain a solution of the carbohydrate or derivative thereof;

(ii) forming a chlorinating agent in and/or combining a pre-formed chlorinating agent in a solvent followed by dissolution of carbohydrate or derivative thereof to obtain a chlorination mixture;

(iii) irreversibly removing all or substantially all of the hydrogen chloride produced during reaction of the chlorinating agent with the hydroxy group or groups of the carbohydrate and/or during chlorination of the carbohydrate or derivative thereof;

(iv) optionally heating the reaction mixture from (iii) under an inert gas atmosphere to a temperature of 60° C. for a period of about 2 hours or more; and (v) optionally heating the reaction mixture to a temperature not more than 100° C., 95° C., or 85° C., for a period of up to 16 hours, to obtain the chlorinated carbohydrate or derivative thereof.

In accordance with an embodiment, the invention also provides a method of preparing sucralose comprising de-esterifying the chlorinated sucrose ester obtained according to the various embodiments described above. The sucrose ester can be de-esterified, for example, by alkaline hydrolysis using sodium methoxide in methanol as shown in U.S. Pat. No. 4,380,476; col. 10, lines 1-22.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following aspects) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the aspects appended hereto as permitted by applicable law. Moreover, any combination of the above-described elements in all possible variations thereof is encompassed by the invention unless otherwise indicated herein or otherwise clearly contradicted by context.

The invention covers the following aspects:

1. A method for chlorinating a carbohydrate or a derivative thereof comprising reacting the carbohydrate or derivative thereof with a chlorinating agent and irreversibly removing hydrogen chloride produced during the chlorination of the carbohydrate or derivative thereof.

2. The method of aspect 1, wherein the carbohydrate or derivative thereof is a sugar or derivative thereof.

3. The method of aspect 2, wherein the sugar derivative is a sugar ester.

4. The method of aspect 3, wherein the sugar ester is a sucrose-6-ester.

5. The method of aspect 4, wherein the chlorinated product obtained is 4,1',6'-trichloro-4,1',6'-trideoxy-6-O-ester of galactosucrose (TGS-6E).

6. The method of any one of aspects 1 to 5, wherein the chlorinating agent is an acid chloride.

7. The method of aspect 6, wherein the acid chloride is selected from the group consisting of thionyl chloride, sulfuryl chloride, phosgene, phosphorus pentachloride, oxalyl chloride, methane sulfonyl chloride, and bis(trichloromethyl) carbonate.

8. The method of any one of aspects 1 to 6, wherein the chlorinating agent is a Vilsmeier Reagent having the formula: [XYC=N$^+$R$_2$] Cl$^-$, wherein X is hydrogen, aryl, or alkyl, wherein the aryl or alkyl is optionally substituted with a halogen, alkoxy, thioalkoxy, amido, or cyano; Y is a leaving group; and R is hydrogen or alkyl which is optionally substituted with halogen, alkoxy, thioalkoxy, amido, or cyano.

9. The method of aspect 8, wherein Y is halogen, heteroalkyl, or a group capable of being displaced by a heteroatomic nucleophile.

10. The method of aspect 9, wherein the heteroatomic nucleophile is selected from the group consisting of tosylate, brosylate, besylate, nosylate, mesylate, alkylfluorosulfonates, triflates, nonaflates, and tresylates.

11. The method of aspect 9, wherein Y is halogen.

12. The method of any one of aspects 8, 9, and 11, wherein X is hydrogen, Y is chloro, and R is methyl.

13. The method of aspect 12, wherein the Vilsmeier Reagent which is produced by the reaction of N,N-dimethylformamide with an acid chloride.

14. The method of aspect 13, wherein the acid chloride is selected from the group consisting of thionyl chloride, sulfuryl chloride, phosgene, phosphorus pentachloride, oxalyl chloride, methane sulfonyl chloride, and bis(trichloromethyl) carbonate.

15. The method of any one of aspects 1 to 14, wherein the chlorination reaction is carried out in a polar or non-polar solvent.

16. The method of aspect 15, wherein the polar solvent is a polar aprotic solvent.

17. The method of aspect 16, wherein the polar aprotic solvent is selected from the group consisting of N,N-dimethylformamide, N,N-dimethylacetamide, N-methyl pyrrolidone, dimethylsulfoxide, sulfolane, glycol ethers, and the like.

18. The method of aspect 17, wherein the polar aprotic solvent is N,N-dimethylformamide.

19. The method of any one of aspects 1 to 18, wherein the chlorination is carried out at a temperature of 100° C. or below.

20. The method of aspect 19, wherein the chlorination is carried out at a temperature of 85° C. or below.

21. The method of aspect 20, wherein the reaction mixture is heated to a temperature not exceeding 85° C. after contacting the carbohydrate with the chlorinating agent.

22. The method of any one of aspects 1 to 21, wherein hydrogen chloride is irreversibly removed from the reaction mixture by an irreversible physical process.

23. The method of aspect 22, wherein the irreversible physical process comprises applying vacuum or sonic energy to, or inducing cavitation into, the reaction mixture, or distilling off solvent with HCl.

24. The method of aspect 23, wherein the vacuum is applied when the reaction is mixture is being heated from a temperature of 50° C. or higher.

25. The method of aspect 24, wherein the vacuum is applied until all or substantially all of the sucrose-6-ester is consumed.

26. The method of any one of aspects 23 to 25, wherein the vacuum is applied for a period of about 5 minutes to about 12 hours.

27. The method of aspect 26, wherein the vacuum is applied for a period of 30 minutes to about 2 hours.

28. The method of aspect 23, wherein the distillation is carried out with or without vacuum.

29. The method of any one of aspects 1 to 21, wherein hydrogen chloride is irreversibly removed from the reaction mixture by an irreversible chemical process.

30. The method of aspect 29, wherein the irreversible chemical process comprises reacting hydrogen chloride with a material that forms a product that contains covalently bonded chlorine atom.

31. The method of aspect 30, wherein the material is a cyclic ether or an olefin.

32. The method of aspect 31, wherein the cyclic ether is propylene oxide.

33. The method of any one of aspects 1 to 32, further comprising providing a moisture free gas atmosphere over the reaction mixture or sparging a moisture free gas through the reaction mixture.

34. The method of aspect 33, wherein the moisture free gas is nitrogen, argon, helium, or air.

35. The method of any one of aspects 1 to 34, further comprising contacting the reaction mixture with an adsorbent for hydrochloric acid.

36. The method of aspect 35, wherein the adsorbent is placed in a scrubbing vessel located external to the chlorinating reactor.

37. The method of aspect 36, wherein the adsorbent comprises an acid scavenger.

38. The method of aspect 36 or 37, wherein the adsorbent or acid scavenger is selected from the group consisting of zeolites, activated carbon, organic amines, and polymeric resins.

39. A method for chlorinating a carbohydrate or a derivative thereof comprising:
(i) dissolving the carbohydrate or derivative thereof in a polar or non-polar aprotic solvent to obtain a solution of the carbohydrate or derivative thereof;
(ii) forming a chlorinating agent in and/or combining a pre-formed chlorinating agent in a solvent followed by dissolution of carbohydrate or derivative thereof to obtain a chlorination mixture;

(iii) irreversibly removing all or substantially all of the hydrogen chloride produced during reaction of the chlorinating agent with the hydroxy group or groups of the carbohydrate and/or during chlorination of the carbohydrate or derivative thereof;

(iv) optionally heating the reaction mixture from (iii) under an inert gas atmosphere to a temperature of 60° C. for a period of about 2 hours or more; and (v) optionally heating the reaction mixture to a temperature not more than 85° C., for a period of up to 16 hours, to obtain the chlorinated carbohydrate or derivative thereof.

40. The method of aspect 39, wherein the irreversible removal of the hydrogen chloride produced during chlorination of the carbohydrate or derivative thereof is carried out by an irreversible physical process and/or an irreversible chemical process.

41. The method of aspect 40, wherein the irreversible removal is carried out in an irreversible physical process.

42. The method of aspect 41, wherein the irreversible physical process comprises applying vacuum or sonic energy or sparging a moisture free gas over the reaction mixture, inducing cavitation into the reaction mixture, or distilling off solvent with HCl.

43. The method of aspect 40, wherein the irreversible removal is carried out in an irreversible chemical process or a physical process carried out external to the chlorinating reactor.

44. The method of aspect 43, wherein the irreversible chemical process comprises reacting the hydrogen chloride with a material that forms an inert chlorinated product.

45. The method of aspect 43, wherein the physical process comprises scrubbing hydrogen chloride on an adsorbent placed in a scrubbing vessel located external to the chlorinating reactor.

46. The method of any one of aspects 39 to 45, wherein the chlorinated carbohydrate or derivative thereof is chlorinated sucrose-6-ester.

47. The method of aspect 46, wherein the chlorinated sucrose-6-ester produced is free or substantially free of charred residues.

48. The method of aspect 46 or 47, wherein the yield of sucralose-6-ester is at least 65%.

49. A method of preparing sucralose comprising de-esterifying the chlorinated sucrose 6-ester obtained according to any one of aspects 1 to 48 to obtain the sucralose.

50. Sucralose prepared by the method of aspect 49, which is free or substantially free of charred impurities.

51. Sucralose prepared by the method of aspect 49, which is free or substantially free of overchlorinated impurities.

The invention claimed is:

1. A method for chlorinating a sucrose-6 ester comprising reacting the sucrose-6-ester dissolved in an N,N-dialkylformamide, an N,N-dialkylacetamide, or N-methylpyrrolidone solvent with a chlorinating agent and irreversibly removing during chlorination at least a portion of the hydrogen chloride produced by the reaction of the chlorinating agent with the sucrose-6-ester, wherein the chlorination is conducted at a temperature of about 50° C. to 100° C., and the hydrogen chloride is irreversibly removed as a combination with the N,N-dialkylformamide, N,N-dialkylacetamide, or N-methylpyrrolidone solvent by vacuum distillation.

2. The method of claim 1, wherein the chlorination is carried out at a temperature of about 60° C. to about 90° C.

3. The method of claim 1, wherein vacuum is applied for a period of about 5 minutes to about 12 hours.

4. The method of claim 1, wherein at least about 40% of the hydrogen chloride is irreversibly removed.

5. The method of claim 1, wherein at least about 50% of the hydrogen chloride is irreversibly removed.

6. The method of claim 1, wherein all or substantially all of the hydrogen chloride is irreversibly removed.

7. The method of claim 1, wherein the N,N-dialkylformamide or N,N-dialkylacetamide solvent is N,N-dimethylformamide or N,N-dimethylacetamide.

8. The method of claim 7, wherein the N,N-dialkylformamide solvent is N,N-dimethylformamide.

9. The method of claim 8, wherein the combination of hydrogen chloride and N,N-dimethylformamide is an azeotrope.

10. The method of claim 1, wherein the sucrose-6-ester is sucrose-6-benzoate ester.

11. The method of claim 1, wherein the sucrose-6-ester is sucrose-6-acetate ester.

12. The method of claim 1, wherein the chlorinated product obtained is 4,1',6'-trichloro-4,1',6'-trideoxy-6-O-ester of galactosucrose (TGS-6E).

13. The method of claim 12, wherein the chlorinated product obtained is 4,1',6'-trichloro-4,1',6'-trideoxy-6-O-benzoate ester of galactosucrose.

14. The method of claim 12, wherein the chlorinated product obtained is 4,1',6'-trichloro-4,1',6'-trideoxy-6-O-acetate ester of galactosucrose.

15. The method of claim 1, wherein the chlorinating agent is an acid chloride selected from the group consisting of thionyl chloride, sulfuryl chloride, phosgene, phosphorus pentachloride, oxalyl chloride, and methanesulfonyl chloride, or the chlorinating agent is bis(trichloromethyl)carbonate.

16. The method of claim 1, wherein the chlorinating agent is an acid chloride.

17. The method of claim 1, wherein the chlorinating agent is a Vilsmeier Reagent having the formula: $[XYC=N^+R_2]$ $Cl^-$, wherein X is hydrogen, aryl, or alkyl, wherein the aryl or alkyl is optionally substituted with a halogen, alkoxy, thioalkoxy, amido, or cyano; Y is a leaving group; and R is hydrogen or alkyl which is optionally substituted with halogen, alkoxy, thioalkoxy, amido, or cyano.

18. The method of claim 17, wherein, in the Vilsmeier Reagent, Y is halogen, heteroalkyl, or a group capable of being displaced by a heteroatomic nucleophile.

19. The method of claim 18, wherein Y is halogen.

20. The method of claim 17, wherein, in the Vilsmeier Reagent, X is hydrogen, Y is chloro, and R is methyl.

21. The method of claim 17, wherein the Vilsmeier Reagent is produced prior to chlorination or in situ during chlorination.

22. A method for chlorinating a sucrose-6ester comprising:

(i) dissolving the sucrose-6-ester in N,N-dimethylformamide, N,N-dimethylacetamide, or N-methylpyrrolidone to obtain a solution of the sucrose-6-ester;

(ii) forming a chlorinating agent in and/or combining a pre-formed chlorinating agent in N,N-dimethylformamide, N,N-dimethylacetamide, or N-methylpyrrolidone and combining the chlorinating agent or the pre-formed chlorinating agent with the solution of sucrose-6-ester obtained in (i) to obtain a chlorination mixture;

(iii) irreversibly removing during chlorination at least a portion of the hydrogen chloride produced by the reaction of the chlorinating agent with the hydroxy group or groups of the sucrose-6-ester, wherein the chlorination is conducted at a temperature of about 50° C. to 100° C., wherein the hydrogen chloride is irreversibly removed as a combination with N,N-dimethylformamide, N,N-dimethylacetamide, or N-methylpyrrolidone by vacuum distillation.

23. The method of claim 22, wherein the combination of hydrogen chloride and N,N-dimethylformamide, N,N-dimethylacetamide, or N-methylpyrrolidone is an azeotrope.

24. The method of claim 22, wherein the sucrose-6-ester is sucrose-6-benzoate ester.

25. The method of claim 22, wherein the sucrose-6-ester is sucrose-6-acetate ester.

26. The method of claim 22, wherein the chlorinated product obtained is 4,1',6'-trichloro-4,1',6'-trideoxy-6-O-benzoate ester of galactosucrose.

27. The method of claim 22, wherein the chlorinated product obtained is 4,1',6'-trichloro-4,1',6'-trideoxy-6-O-acetate ester of galactosucrose.

* * * * *